United States Patent [19]

Bystryn

[11] Patent Number: 5,635,188
[45] Date of Patent: Jun. 3, 1997

[54] ANTI-CANCER VACCINE

[76] Inventor: Jean-Claude Bystryn, 560 First Ave., New York, N.Y. 10016

[21] Appl. No.: 367,682

[22] Filed: Dec. 30, 1994

Related U.S. Application Data

[63] Continuation of Ser. No. 210,243, Mar. 18, 1994, abandoned, which is a continuation of Ser. No. 717,972, Jun. 20, 1991, abandoned, which is a continuation of Ser. No. 485,780, Feb. 22, 1990, Pat. No. 5,030,621, which is a continuation of Ser. No. 41,864, Apr. 23, 1987, abandoned.

[51] Int. Cl.$^6$ .............................. A01K 39/00; C07K 14/47
[52] U.S. Cl. .................... 424/277.1; 530/350; 530/395; 514/2; 514/8; 514/12
[58] Field of Search .................. 424/277.1; 530/350, 530/395; 514/2, 8, 12

[56] References Cited

U.S. PATENT DOCUMENTS

| | | | |
|---|---|---|---|
| 4,108,983 | 8/1978 | Wallack | 424/88 |
| 4,415,553 | 11/1983 | Zhabilov et al. | 424/88 |
| 5,030,621 | 7/1991 | Bystryn | 514/21 |
| 5,141,742 | 8/1992 | Brown et al. | 424/186.1 |
| 5,308,614 | 5/1994 | Hakomori | 424/277.1 |

FOREIGN PATENT DOCUMENTS

| | | | |
|---|---|---|---|
| 133566 | 1/1979 | Germany | 530/806 |

OTHER PUBLICATIONS

Lloyd, Annal of NY Acad. of Sci, 690, 51–58, 1993.
Livingston et. al., Cancer, 55 713–720, Feb. 1985.
CA 73: 85933m, Zalula, 1970.
CA 73: 85940m, Rand Dev. Corp, 1970.
CA 89: 4357g, Ng et al, 1978.
CA 84: 173965f, Gautam et al, 1976.
Chirigos et al, Cancer Res, 34, 1085–1091, 1978.
Seigler et al, Ann Surg, 190(3), 366–372, Sep. 1979.
Kataoka et al, Cancer Res, 40, 3839–3845, Oct. 1980.
Livingston et al, Cancer, 55, 713–770, Feb. 1985.
CA 91: 37350u, Ray et al, 1979.
Wright et al, *Cancer Res*, 37, 4228–4232, Nov. 1977.
Reisfield et al, Cancer Res, 39, 2860–2865, Aug. 1977.
Kessler et al, Cancer Res, 38, 1041–1048, Apr. 1978.
Leung et al, J. Immunol., 119(2), (1977), pp.164–670.
Chem Ab 93: 43610m, Kamiyama et al, 1980.
CA 93 43566b, Kataoka, 1980.
CA 93: 19533y, McCollester, 1980.

*Primary Examiner*—Lila Feisee
*Assistant Examiner*—Julie E. Reeves
*Attorney, Agent, or Firm*—Cooper & Dunham LLP

[57] ABSTRACT

A human anti-cancer vaccine is prepared by culturing human cancer cells, such as human melanoma cells, in a serum-free medium. The cancer cells are selected on the basis of expressing different patterns of cell surface tumor antigens and are adapted and grown in a serum-free medium. During culturing, cell surface antigens of the cancer cells are shed into the culture medium. The culture medium, after removal of the cancer cells, containing the shed cancer cell antigens is concentrated. When used as an anti-cancer vaccine, the resulting concentrated composition is administered to the patient, such as intradermally. In the instance where patients are cancer patients, the vaccine is administered to the patient intradermally over a period of weeks with or without an adjuvant.

9 Claims, No Drawings

ANTI-CANCER VACCINE

This is a continuation of application Ser. No. 08/210,243, now abandoned filed Mar. 18, 1994 which, in turn, is a continuation of Ser. No. 07/717,972 filed Jun. 20, 1991, now abandoned which, in turn, is a continuation of Ser. No. 07/485,780 filed Feb. 22, 1990 (U.S. Pat. No. 5,030,621) which, in turn, is a continuation of Ser. No. 07/041,864 filed Apr. 23, 1987, now abandoned.

BACKGROUND OF THE INVENTION

This invention relates to human vaccines, such as vaccines for protection against pathogenic microorganisms, e.g. bacterial infections and the like, and to human anti-cancer vaccines. More particularly, and in one special embodiment, this invention relates to the preparation of human anti-cancer vaccines useful for the prevention and/or treatment of cancer, such as melanoma, breast cancer, colon cancer, lung cancer and other such cancers.

For the treatment of cancer, it has been suggested to increase tumor protective immunity by active immunization to tumor antigens, see (1) the article by R. K. Oldham entitled "Biologicals and Biological Response Modifiers: Fourth Modality of Cancer Treatment", *Cancer Treat Rep* (1984);68:221–232, and (2) the article by M. J. Mastrangelo et al entitled "Current Condition and Prognosis of Tumor Immuunotherapy: A Second Opinion", *Cancer Treat Rep* (1984);68:207–219. Unfortunately, this approach for the prevention and/or treatment of cancer has not been successful or completely satisfactory because of a number of problems, such as the absence in the vaccine of tumor antigens expressed by the tumor to be treated, poor characterization of the antigens in tumor vaccines, the contamination of vaccines by immunogenic but undesirable material, such as fetal calf serum (FCS) protein or transplantation antigens and additionally due to the antigenic heterogenicity of the cancer cells. Moreover, such tumor vaccines were often prepared from fresh tumor cells, the supply of which is limited so that the properties of the vaccines are not reproducible.

A clinical trial was conducted to evaluate the toxicity and immunogenicity in man of a partially purified, polyvalent, melanoma antigen vaccine and some success was indicated, see the abstract of the paper by J. C. Bystryn et al published by *The Society for Investigative Dermatology, Inc.* entitled "Phase 1 Trial of Specific Immunotherapy of Melanoma with a Polyvalent Melanoma Antigen Vaccine"

It is an object of this invention to provide an improved anti-cancer vaccine.

It is another object of this invention to provide a technique for the preparation of an improved anti-cancer vaccine.

It is another object of this invention to provide an immunotherapy for the prevention and/or treatment of human cancer.

Yet another object of this invention is to provide a technique for the production of reproducible anti-cancer vaccines.

Still another object of this invention is to provide a technique for the preparation of an anti-cancer vaccine useful when introduced into a patient to prevent and/or to treat cancer.

It is still another object of this invention to provide a technique for the preparation of vaccines for diseases caused by infectious cellular and/or subcellular organisms and/or viruses.

It is yet another object of this invention to provide a technique for the preparation of clinically or biologically important material shed from the surface of cells and the like.

How these and other objects of this invention are achieved will become apparent in the light of the accompanying disclosure. In at least one embodiment of the practices of this invention at least one of the foregoing objects will be achieved.

SUMMARY OF THE INVENTION

A human vaccine useful for the prevention and/or treatment of infections caused by pathogenic microorganisms, including vital, fungal, protozoal, amoebic and bacterial infections and the like, human cancer, including human melanoma, a skin cancer, human lung cancer, human breast cancer, human colon cancer and other human cancers is produced. For the production of a human cancer vaccine, the vaccine is produced by culturing human cancer cells, such as human melanoma cells, in a serum-free medium for the collection in the medium of cancer antigens, such as multiple melanoma associated antigens (MAAs). The vaccine produced from the shed material contains multiple cell surface antigens including tumor antigens and if prepared from cells adapted to and grown in a serum-free medium, is free of calf serum proteins. The use of bioreactors for the bulk culture of the cells and the like for vaccine production is particularly useful.

The vaccine is employed for the prevention and/or treatment of cancer in humans by administering the vaccine into the extremities of the patient a number of times a month and then once every few months thereafter for an extended period of time, such as 1–4 years, more or less. As indicated, the invention is applicable for the production of vaccines for the prevention and treatment of other cancers as well as for infectious diseases caused by bacteria, fungi, rickettsia, virus and other cellular and subcellular organisms.

DETAILED DESCRIPTION OF THE INVENTION

The practices of this invention are hereinafter described in some detail with respect to the production of a human melanoma antigen vaccine and the treatment of melanoma patients. As indicated hereinabove, however, the practices of this invention are also applicable to the production of a human lung cancer vaccine, a human breast cancer vaccine, a human colon cancer vaccine and other human cancer vaccines as well as vaccines for infectious diseases, particularly infectious diseases caused by bacteria, fungi and other microorganisms.

In the preparation of a human melanoma antigen vaccine in accordance with this invention the vaccine was prepared from material shed by four lines of human melanoma cells: HM31, RM34, HM49, and SK-Mel-28. The cells were selected on the basis of the cells expressing different patterns of all surface melanoma antigens and adapted to and maintained in serum-free medium, see the article by J. P. Mather et al entitled "The Growth of Mouse Melanoma Cells in Hormone Supplemented Serum-Free Medium", *Exp Cell Res* 1979;120:191–200, for at least 8 weeks prior to use.

Antisera

A panel of eight murine monoclonal antibodies and two rabbit polyclonal melanoma antisera were used for MAA immunophenotyping. The antigens defined are listed in accompanying Table 1. The antigens defined by the murine and rabbit antisera are different, even though some may have similar molecular weights, as shown by variations in their distribution among melanomas (Table 3). The antisera to Dr antigens and FCS were obtained commercially.

Vaccine Preparation

Melanoma cells were incubated at a concentration of $2 \times 10^6$/ml serum-free RPMI 1640 medium. After 3 hours at 37° C., the medium was collected and the cells were removed by centrifugation at 2,000 g for 10 minutes, and larger particles were removed by recentrifugation at 12,000 g for 15 minutes. Equal volumes of medium from the four cells lines were pooled, concentrated 10-fold by vaccum ultrafiltration and made up to a final concentration. In some cases vaccines were prepared with further treatment including the addition of a surfactant, e.g. 0.5% Nonidet P-40 (NP-40) and 0.02% sodium azide, and then ultracentrifuged at 100,000 g for 90 minutes. The supernatant was dialyzed at 4° C. against normal saline with 0.02% sodium azide and made up to the desired protein concentration by the addition of normal saline, passed through a 0.1 um Millex Millipore filter to remove microorganisms; and 0.5 ml aliquots dispensed into sterile, pyrogen-free glass vials. The vials were stored at −70° C. until used.

A control vaccine was similarly prepared from a pool of normal peripheral leukocytes obtained from five normal individuals. Prior to use, the vaccine was tested for aerobic and anerobic bacteria, fungi, and hepatitis antigen and also tested for mycoplasma by bisbenzamide DNA fluorochrome stain and for pyrogens by the limulus test. For MAA phenotyping, the vaccine was prepared from cells radioiodinated by the lactoperoxidase technique, see the article by J. C. Bystryn et al entitled "Identification and Solubilization of Iodinated Cell Surface Human Melanoma Associated Antigens", *Int J Cancer* 1977;20:165–172, and radiolabeled cells were lysed in 10 ml of 0.05 NP-40.

Assays

Protein concentration was measured by the Lowry method, see the article by O. H. Lowry et al entitled "Protein Measurement with the Folinphenol Reagent", *J Biol Chem* 2951;193:265–275. Profiles of proteins were analyzed by SDS-PAGE and silver staining or autoradiography, see the articles, respectively, by J. C. Bystryn entitled "Comparison of Cell-Suface Human Melanoma Associated Antigens Identified by Rabbit and Murine Antibodies", *Hybridoma* 1982;4:465–472, and B. R. Oakley et al "A Simplified Ultrasensitive Silver Stain for Detecting Proteins in Polyacrylamide Gels", *Anal Biochem* 1980;105:361–363. Radioactivity associated with labeled macromolecules was measured by precipitation with 10% trichloroacetic acid. MAAs were assayed by protein A-sepharose immunoprecipitation of labeled antigens by using the panel of antisera listed in Table 1, followed by SDS-PAGE and autoradiography. FCS proteins and Dr antigens were assayed in a similar manner by using appropriate antisera.

Clinical Studies

The vaccine was used to immunize 13 patients with metastatic malignant melanoma, see accompanying Table 4. All had intact immune function, as evidenced by skin reactivity to at least one standard recall antigen or by the ability to be sensitized to dinitrochlorobenzene (DNCB). A single lot of vaccine was used to treat all patients. Therapy was initiated at least 1 month following surgery, chemotherapy, or radiation therapy. No other therapy was given concurrently, and 0.1 ml of vaccine was administered without adjuvant into each of the four extremities weekly for eight weeks, monthly for three months, then twice at three month intervals and thereafter every six months. The initial dose of 0.25 ug/site was increased every 2 weeks to 1.0, 10.0 and 50 ug/site. Physical examination, blood count, sedimentation rate, serum chemistry profile, urinalysis, serum immunoelectrophoresis, immune complex levels, and chest x-ray were performed prior to therapy, twice monthly and every 2 months thereafter. Chest x-rays were repeated every 3 months and other radiological studies as indicated. Serum for melanoma antibody was collected on two occasions prior to therapy and prior to each vaccination.

Immune Responses to Melanoma

Antibodies to melanoma surface antigens were assayed by indirect immunoprecipitation, using as antigen detergent extracts of lactoperoxidase radiodinated melanoma cells see the article by G. K. Naughton et al entitled "Antibodies to Normal Human Melanocytes in Vitiligo", *J Exp Med* 1983;158:246–251. The cells were those used for vaccine production. Each patient served as his own control. Immunization was considered to have increased melanoma antibody level if the counts per minute (cpm) immunoprecipitated by postimmune sera were at least 50% greater than the average cpm immunoprecipitated by two preimmune sera in the same patient. The antigens defined by antibody in selected patients were identified by sodium dodecyl sulfate-polyacrylamide gel electrophoresis (SDS-PAGE) and autoradiography, see reference 11 hereinabove. Antibodies of FCS proteins in rabbit and human sera were assayed by protein A-sepharose immunoprecipitation using fetal calf serum radioiodinated with immobilized lactoperoxidase, see the article by G. S. David entitled "Protein Iodination with Solid State Lactoperoxidase", *Biochemistry* 1974;13:1014–1021.

Cellular immunity to melanoma was evaluated by delayed-type hypersensitivity (DTH) reactions to skin tests with 10 ug of vaccine. These were considered positive if induration at least 10 mm in average diameter persisted for 24–48 hours.

Protein Profile of Vaccine

At least 20 proteins ranging in MW 30 Kd to 70 Kd were present in the vaccine as indicated by SDS-PAGE profile of proteins stained with silver in the material shed by pooled melanoma cell s. Additional proteins with MWs ranging to 200 Kd could be visualized in vaccine prepared from radioiodinated cells upon SDS-PAGE profile of MAAs in vaccine prepared from radioiodinated cells immunoprecipitated by monocloncal antibodies.

To minimize the presence of FCS proteins in the vaccine, the vaccine was prepared from cells maintained in serum-free medium for at least 8 weeks. Some experiments confirmed that no detectable FCS proteins persisted in the vaccine. None could be detected by immunoprecipitation with anti-FCS serum in vaccine prepared from lactoperoxidase radioiodinated cells, even though this procedure is sensitive enough to detect FCS adhering to and shed by melanoma cells grown in the presence of serum, see the article by J. C. Bystryn et al entitled "Release of Surface Macromolecules by Human Melanoma and Normal Cells", *Cancer Res* 1981;41:910–4. Two rabbits repeatedly immunized to the vaccine developed antibodies to a number of melanoma antigens in the vaccine but not to radioiodinated FCS proteins. By contrast, antibodies to FCS were readily detected in two control rabbits immunized in parallel to vaccine contaminated with trace amounts of xenogeneic serum. Finally, no antibodies to FCS were found in 13 patients repeatedly immunized to the vaccine.

To separate MAAs from transplantation antigens, shed material was treated with 0.5% NP-40 to solubilize aggregates and was subsequently ultracentrifuged. The effects of this procedure on proteins, tumor, and transplantation antigens are summarized in Table 2. Ultra-centrifugation of shed material not treated with detergent removed much of the radioactivity associated with labeled macromolecules, in addition to those MAAs defined by polyclonal antiserum SB29 and 100% of those associated with Dr antigens. Ultracentrifugation of detergent-treated shed material still resulted in a loss of all detectable Dr antigens but reduced the loss of labeled macromolecules to 17% and of MAAs to 30%. Thus, detergent treatment and ultracentrifugation removed Dr antigens with an acceptable loss in MAAs.

Antigenic Properties of Vaccine

Vaccine prepared from radioiodinated cells was immunophenotyped with a panel of 10 melanoma antisera. The results are summarized in Table 1. Most of the MAAs tested were present in the vaccine. Three batches of vaccine prepared several months apart all contained the MAAs tested, see accompanying Table 1. Upon freeze-thawing three times or storage at $-70°$ C. for four months, there was no loss in antigenic activity.

Distribution of MAAs in Various Melanomas

Because it is desirable that the vaccine contain at least one tumor antigen which will be present on most of the melanoma tumors to be treated, it was examined whether or not the panel of MAAs in the vaccine satisfied this requirement. Fifteen melanomas were lactoperoxidase radioiodinated and immunophenotyped for the MAAs present in the vaccine. There were marked differences, see accompanying Table 3, in the pattern of MAAs expressed by each melanoma. However, all the melanomas expressed several of the MAAs present in the vaccine.

Phase I Trial

Thirteen patients with metastatic melanoma were immunized with increasing doses of vaccine for 2 months, see accompanying Table 4, and 10 of these received 2 to 10 additional booster doses during the period 5 months to 2 years. No toxicity was observed other than transient urticaria at the site of injection. A similar urticarial reaction occurred in the skin of each of five patients tested with sterile saline containing an amount of NP-40 equal to that present in the vaccine. There was no reaction to skin tests to sterile saline alone.

Additional Clinical Trials

Clinical studies were performed to determine the toxicity of the vaccine in patients with early melanoma and the effect of several immunization strategies on immunogenecity. A total of 55 melanoma patients (36 with Stage II disease metastatic to regional nodes and 19 patients with Stage III widely disseminated disease) have been treated. There was no toxicity other than transient inflammation at the site of vaccine injection.

Immune Response to Immunization

Antibodies to surface antigens on melanoma cells, assayed by indirect immunoprecipitation, increased in five (38%) patients, see accompanying Table 5. The increase was usually small, although in one patient (patient 1) peak binding activity was 300% greater than the preimmune level. Antibody levels increased in some patients within 1 week following the first immunization, suggesting that a secondary type of immune response was elicited. The immunogenic antigens that stimulated the production of melanoma antibodies were identified in three patients by SDS-PAGE and autoradiography. These were proteins with MWs of about 75, 85, and 200+ Kd. The larger antigen appeared to be more immunogenic, since all three patients developed antibodies to it, whereas antibodies to the other two antigens were present in only one patient. None of these antigens was related to FCS proteins, since their binding was not blocked by excess cold FCS. Furthermore, after 2 months of immunization, there was no increase in antibodies to FCS in any of the patients, see accompanying Table 6.

Cellular immunity to melanoma, evaluated by DTH reaction to skin tests with the vaccine, was induced in four (31%) patients, see accompanying Table 5. Skin tests were negative prior to immunization in all patients. Three to six immunizations with 10 ug or more of vaccine were required to induce a positive reaction. There was no reaction in positive patients to skin tests with equal amounts of human albumin or to a control vaccine prepared from pooled normal peripheral leukocytes. Overall, there was an increase in humoral and/or cellular immune response to melanoma following immunization in eight (62%) of the patients.

In subsequent clinical trial s it was found that antibody and/or cellular immune responses to melanoma were induced more frequently in Stage II (69% of 36 patients) than in Stage III (53% of 19 patients) disease. The ability of different immunization schedules, alum or pretreatment with low dose cyclophosphamide, to potentiate immunogenicity was compared after 2 months of immunization. Bi-weekly immunization with a fixed intermediate dose of vaccine was more immunogenic than weekly immunization with escalating vaccine doses. Alum increased slightly the intensity of cellular responses while pretreatment with cyclophosphamide augmented slightly both the incidence and intensity of cellular immune responses. There was a reciprocal relationship between the induction of humoral and cellular immune responses. The most effective immunization schedule consisted of pretreatment with cyclophosphamide which augmented antibody and/or cellular immune responses to melanoma in 83% of patients.

The vaccine is capable of augmenting immune responses to a patient's own tumor. There were examined the density and distribution of lymphocytic inflammatory cells in cutaneous metastases that developed during the course of vaccine immunization in 11 patients and comparison was made in a blinded fashion to the lymphocytic infiltrate present in similar cutaneous melanoma metastases removed from 22 non-immunized, randomly selected patients. Dense cellular infiltrates (15 lymphoid cells/HPF) were more frequent in tumor nodules of immunized patients (10 of 11 nodules, 91%) than in those of control patients (9 of 22 nodules, 41%), p 0.01. The cells were more likely to be infiltrating within the tumornodules in immunized patients (7 of 11 nodules, 64%) than in control patients (5 of 22 nodules, 23%), p 0.05. The incidence of lymphoid cells at the periphery of nodules was similar in both groups.

These results indicate that immunization to melanoma vaccine can augment lymphocyte infiltration into tumors in vivo, and suggests that polyvalent allogeneic melanoma vaccines can boost a patient's ability to mount an immune response to his own tumor.

Effect of Immunization on Tumor Growth

In the initial Phase I study, two of the 13 immunized patients have done well, see accompanying Table 4. There was a complete remission in a 46-year-old male (patient 10) who developed three disseminated cutaneous metastasis one year following excision of a melanoma of the right upper back. Two metastases were removed and the third left as a marker. It increased in size 30% during the first months of immunotherapy, was stable for several months, and then slowly decreased in size by 50%. It was removed 10 months after onset of immunotherapy and histologically was a regressed malignant melanoma with only pigment-laden macrophages at the site. The patient is currently disease-free, 24 months after onset of immunotherapy.

There was a long-term stable disease in a 75-year-old woman (patient 9) who developed two cutaneous metastases 2 years after excision of a malignant melanoma of the right calf. These were removed, and she was treated with dimethyltriazenoimidozole carboxamide (DTIC) and actinomycin D. Three years later, six new cutaneous metastases appeared, and she was started on vaccine immunotherapy. Cutaneous metastases increased in number and size during the next 4 months until she had 15. She was continued on immunotherapy, and there has been no further increase in size or number of metastases. The largest lesion regressed spontaneously 6 months after onset of immunotherapy. The patient currently has stable disease 14 months after onset of immunotherapy.

In other studies, it was found that recurrence of melanoma was less common in patients with a cellular immune response to the vaccine (35%) than in those with an antibody response (86%) p 0.05 and the disease free interval was prolonged from about 39 to greater than 100 weeks. These results suggest that active immunization to the melanoma vaccine can slow the progression of melanoma in some patients.

Several features of the technique used to prepare the vaccine deserve attention, because they were designed to minimize problems. The vaccine was prepared from melanoma cells grown in serum-free medium to avoid contamination with FCS proteins. These proteins are highly immunogenic and responsible for most immune responses induced by human tumor vaccines prepared from cultured cells, see the articles by P. O. Livingston et al entitled "Serological Responses of Melanoma Patients to Vaccines Derived from Allogenic Cultured Melanoma Cells", *Int J Cancer* 1983;31:567–575, P. O. Livington et al entitled "Serological Response of Melanoma Patients to Vaccines Prepared from VSV Lysates of Autologous and Allogenic Melanoma Cells", *Cancer* 1985:55–713–720 and M. S. Mahaley, Jr. et al entitled "Immunobiology of Primary Intracranial Tumors. Part 8: Serological Responses to Active Immunization of Patients with Anaplastic Gliomas", *J Neurosurg* 1983;59:208–216. This approach appears to have been successful, since no FCS proteins were detectable in the vaccine by direct assay or by the more sensitive method of looking for an immune response to these proteins in animals or persons immunized to it.

Cultured cells were used to ensure a continued and reproducible source of material, a basic requirement for vaccine development, see reference article 1. Three batches of vaccine prepared several months apart all contained the MAAs that were tested for, indicating that vaccine containing similar antigens can be made reproducilibly. Quantitative changes in the amount of each antigen in the vaccine have not been excluded.

The vaccine was prepared from a pool of cells, selected because they expressed different patterns of surface MAAs. This was done to create a polyvalent vaccine, which is desirable in treating melanoma cells (and, indeed, for treating other cancer cells) that are antigenically heterogeneous, see the articles by J. C. Bystryn et al entitled "Immunophenotype of Human Melanoma Cells in Different Metastases", *Cancer Res, in press,* 1985, M. Y. Yeh et al entitled "Clonal Variation in Expression of a Human Melanoma Antigen Defined by a Monoclonal Antibody", *J Immunol* 1981;126:1312–7, A. P. Albino et al entitled "Heterogeneity in Surface Antigen and Glycoprotein Expression of Cell Lines Derived from Different Melanoma Metastases of the Same Patient", *J Exp Med*. 1981;154–1764–1778. The vaccine contained multiple MAAs. Most of the MAAs tested for were present in the vaccine; it is therefore likely that the vaccine contains additional MAAs that were not tested for. At least one of the MAAs present in the vaccine was expressed by each of 15 metastatic melanomas that were immunophenotyped. Thus, a mixture of tumor antigens in the vaccine would be appropriate to circumvent antigenic heretogeneity among melanomas.

Shed antigens were used because they are partially purified. They are separated from the bulk of cytoplasmic components, which are slowly released (5%) during the short collection period; surface components, however, are released rapidly, see the article by J. C. Bystryn et al entitled "Shedding and Degradation of Cell-Surface Macromolecules and Tumor-Associated Antigens by Human Melanoma". *In: Reisfeld R. A,, Ferrone S, eds. Melanoma Antigens and Antibodies, New York: Plenum Press,* 1982:37–52. In addition, shed material is enriched in surface antigens which are more likely to be relevant for immunotherapy and can be repeatedly harvested from the same cells, thus reducing culture requirements.

Finally, detergent treatment and ultracentrifugation were used to separate tumor from Dr antigens. Much of the material shed by melanoma cells is contained in fragments that are sedimented by ultracentrifugation. Treatment with detergent breaks up these fragments so that most tumor antigens remain in suspension following ultracentrifuation, however, as found and confirmed by others, see the article by R. A. Reisfeld et al entitled "Approaches for the Isolation of Biologically Functional Tumor-Associated Antigens", *Cancer Res* 1977;37:2860–2865, ultracentrifugation still causes sedimentation of detergent-treated transplantation antigens. This consequently provides a simple way of separating transplantation from tumor antigens.

The vaccine produced was found to be safe and immunogenic in 55 patients with metastatic melanomas. There was no toxicity other than transient urticaria at the site of the injection. Immune responses to melanoma were induced or augmented in 64% of the patients. Cellular immunity was induced in 51% of the patients. The reaction seemed directed to melanoma, since there was no response to concurrent skin tests with equal amounts of control vaccine prepared from pooled allogenic peripheral leukocytes or to human albumin. The cellular response was induced, rather than preexisting or due to an irritant in the vaccine, since there was no reaction to the initial injections of vaccine at doses that subsequently led to strong skin reactions.

Humoral immunity to melanoma was increased in 24% of patients. The responses were generally weak; however, a major immunogenic contaminant in prior vaccine prepared from cultured cells, i.e. FCS proteins, see the article by H. F. Seigler et al entitled "Specific Active Immunotherapy for Melanoma", *Ann Surg;* 1979;190:366–372, appears to have been successfully removed. No patient developed FCS antibodies, and by blocking studies with cold FCS, the melanoma antibodies induced in some patients were not directed to FCS. The immunogenic antigens in the vaccine were surface proteins with MWs of about 75, 85, and 200+ Kd. As determined by migration on SES-PAGE, these were different from HLA or Dr antigens, whose MW is 50 Kd.

Three of the 19 patients with Stage III disease did well following immunization. One had complete biopsy proven regression of metastatic cutaneous disease and remained healthy and free of melanoma 35 months after starting immunization. Another remained disease-free following resection of a solitary gall bladder metastases 13 months after starting vaccine therapy. The third patient showed a dramatic slowing of previously rapidly progressing cutaneous disease following initiation of vaccine immunotherapy of progression of cutaneous metastases resumed after 6 months bvut the patient remained otherwise healthy and fully active 25 months after starting immunization.

These results are unexpected since immunotherapy is not thought to be effective in patients with advanced dieases, see the article by R. K. Oldham et al entitled "Immunotherapy of the Old and the New", *J Biol Response Mod* 1983;2:295–309. However, because the number of patients is small and the course of melanoma is usually unpredictable, it is difficult to judge the significance of these favorable responses in patients with advanced melanoma.

In patients with less advanced Stage II melanoma, the vaccine appears to be capable of slowing the progression of melanoma in some cases. Recurrences were lower and disease free interval was prolonged in 20 of 45 patients with Stage II melanoma who developed a cellular immune response to the vaccine. These differences were statistically significant.

The availability of a characterized polyvalent melanoma antigen vaccine that can be reproducibly made, safe to use, and immunogenic, should permit a systematic study of the factors that influence the effectiveness of active, specific immunotherapy of melanoma.

Other details of the practices of this invention described hereinabove are to be found in the article by J. C. Bystryn et al entitled "Preparation and Characteristics of a Polyvalent Human Melanoma Antigen Vaccine", *Journal of Biological Response Modifiers* 1986;5:211–224. Also of interest for more details of the practices of this invention is the to be published article by J-C Bystryn et al entitled "Immunogenecity of a Polyvalent Melanoma Antigen Vaccine in Man", the article by M. Dugan et al entitled "Relationship between Immune Responses to Melanoma Vaccine Immunization and Tumor Regression in Man, Kaplan Cancer Center, NYU School of Medicine, New York, N.Y., published in *American Federation for Clinical Research*, 1987 and the article by R. Oratz et al entitled "Induction of Lymphocytic Cell Infiltrate on Human Melanoma Nodules by Active Immunization to Melanoma Antigen Vaccine" to be published by AACR 1987.

In the description of the invention set forth hereinabove, emphasis has been placed upon the preparation of a vaccine useful for the prevention and/or treatment of melanoma. It is clearly indicated, however, that the concept and practices of this invention are generally applicable to the preparation of vaccines to treat or prevent human cancers and for the preparation of vaccines to treat or prevent infectious diseases in man and animals.

The subject invention involves in a special embodiment, an immunotherapeutic approach for the prevention and/or treatment of cancer and infectious diseases. The administration to a patient of a vaccine in accordance with this invention for the prevention and/or treatment of cancer can take place before or after a surgical procedure to remove the cancer, before or after a chemotherapeutic procedure for the treatment of cancer, and before or after radiation therapy for the treatment of cancer and any combination thereof. It would appear, therefore, that the cancer immunotherapy in accordance with this invention would be a preferred treatment for the prevention and/or for the treatment of cancer, particularly since the risk and side effects involved are substantially minimal compared with the other treatments, e.g. surgery, chemotherapy and radiation therapy. A unique aspect of this invention is that the vaccines have the potential or capability to prevent cancer in individuals without cancer but who are at risk of developing cancer.

The administration of a cancer vaccine prepared in accordance with this invention, is generally applicable to the prevention or treatment of cancer. Cancers which could be suitably treated in accordance with the practices of this invention include cancers of the lung, breast, ovary, cervix, colon, head and neck, pancreas, prostate, stomach, bladder, kidney, bone liver, esophagus, brain, testicle, uterus and the various leukemias and lymphomas.

The vaccines in accordance with this invention, like the above-described melanoma vaccines, would be derived from the tumor or cancer cells to be treated. For example, in the treatment of lung cancer in accordance with the practices of this invention, the lung cancer cells would be treated as described hereinabove to produce a lung cancer vaccine. Similarly, breast tumor or cancer vaccine, colon cancer vaccine, pancreas cancer vaccine, stomach cancer vaccine, bladder cancer vaccine, kidney cancer vaccine and the like would be produced and employed as immunotherapeutc agents in accordance with the practices for the prevention and/or treatment of the tumor or cancer cell from which the vaccine was produced.

Vaccines in accordance with this invention could, as stated, also be prepared to treat various infectious diseases which affect man and animals by collecting the relevant antigens shed into the culture medium by the pathogen. As there is heterogenecity in the type of immunogenic and protective antigens expressed by different varieties of organisms causing the same disease, polyvalent vaccines could be prepared by preparing the vaccine from a pool of organisms expressing the different antigens of importance.

In the practices of this invention set forth hereinabove for the treatment of melanoma, the vaccine was intradermally or subcutaneously administered to the extremities, arms and legs, of the patients being treated. Although this approach is generally satisfactory for melanoma and other cancers, including the prevention or treatment of infectious diseases, other routes of administration, such as intramuscularly or into the blood stream may also be used. In addition, the vaccine can be given together with adjuvants and/or immuno-modulators to boost the activity of the vaccine and the patient's response.

The vaccines of this invention, as described hereinabove, have been prepared from cells grown in flasks. The production of the vaccine can, if desired, be scaled up by culturing the cells in bioreactors or fermentors or other such vessels or devices suitable for the growing of cells in bulk. In such apparatus the culture medium would be collected regularly, frequently or continuously to recover therefrom the cell-shed or tumor-shed or materials or antigens before such materials or antigens are degraded in the culture medium.

If desired, devices or compositions containing the vaccine or antigens produced and recoveed in accordance with this invention and suitable for sustained or intermittent release could be, in effect, implanted in the body or topically applied thereto for the relatively slow release of such materials into the body.

In summary, the essential features of vaccine preparation in accordance with this invention are the following:

(a) The use of cultured cells to provide a continued and reproducible supply of material for vaccine production.

(b) The use of a pool of cell lines. Each line is selected on the basis of it expressing a different pattern of cell surface antigens. This is done to ensure that the vaccine contains a broad representation of different antigens, hence, circumventing the problem antigenic heterogeneity of tumor cells.

(c) Adapting and maintaining the cells in serum-free medium. This excludes from the vaccine undesirable and higly immunogeneic fetal calf serum proteins shown to be free of hepatitis, AIDS, and other undesirable pathogens.

(d) Using shed material to obtain antigens for vaccine preparation. This provides numerous advantages. It greatly simplifies the process of collecting bulk, on-line, production of antigens. The antigens which are collected are solubilized. They are also partially purified as they are separated from the bulk of cytoplasmic cellular components which are shed much more slowly. This greatly simplifies subsequent purification or other biochemical procedures. Lastly, shed material permits the antigens to be harvested from the cells without cell destruction. This greatly reduces the cost of cell culture requirements and hence the time and cost of making the vaccine. The continued use of the same cells to generate antigens also greatly reduces cell culture requirements.

The other steps in vaccine preparation can be individualized to satisfy the requirements of particular vaccines. In the case of melanoma vaccines the shed material is concentrated and in some cases treated with detergent and ultracentrifuged to remove transplantation alloantigens.

The disclosures of all the above-identified reference publications are herein incorporated and made part of this disclosure.

As would be apparent to those skilled in the art in the light of the foregoing disclosure, many modifications, alterations and substitutions are possible in the practices of this invention without departing from the spirit or scope thereof.

TABLE 1

MAA immunophenotyping of melanoma vaccine

| Antisera | MAA defined (kilodaltons) | Presence of MAA (vaccine batch) | | | Ref. |
|---|---|---|---|---|---|
| | | 1 | 2 | 3 | |
| Mouse monoclonal | | | | | |
| 225.28S | 240 + | + | + | + | 23 |
| 9.2.27 | 240 + | + | + | + | 24 |
| 436.G10 | 122–130 | 0 | NT[b] | NT | |
| Nu4B | 26, 29, 95, 116 | + | NT | NT | 25 |
| 376.96 | 94 | 0 | NT | NT | 17 |
| 118.1 | 94–97 | + | + | + | 15 |
| 465.12S | 94 | 0 | NT | NT | 27 |
| MeTBT | 69–70 | 0 | NT | NT | 26 |
| Rabbit polyclonal | | | | | |
| SB29, SR54 | 240 | + | + | + | 11 |
| SB29, SR54 | 150[a] | + | + | + | 11 |
| SB29, SB54 | 140[a] | 4 | + | + | 11 |
| SB29, SB54 | 120 | + | + | + | 11 |
| SB29, SB54 | 95 | + | + | + | 11 |
| SB29, SB54 | 75 | + | + | + | 11 |

[a]Not reactive wilh SB54.
[b](NT) not tested.

TABLE 2

Effect of detergent and ultracentrifugation on macromolecules, MAAs, and Dr antigens in material shed by melanoma cells

| Treatment[a] | $^{125}$I-macromolecules[b] | | $^{125}$I-MAAs[c] | | $^{125}$I-Dr[c] | |
|---|---|---|---|---|---|---|
| | cpm | Change[d] (%) | cpm | Change (%) | cpm | Change (%) |
| None | 10,362 | | 817 | | 428 | |
| Ultracentrifugation | 6,325 | −40 | 258 | −70 | 0 | −100 |
| NP-40 + ultracentrifugation | 8,612 | −17 | 574 | −30 | 0 | −100 |

[a]Material shed by radioiodinated melanoma cells was ultracentrifuged in 0.5-ml aliquots at 100,00 g for 90 min, incubated in a final concentration of 0.5% NP-40 for 2 h prior to ultracentrifugation, or not treated. All were subsequently assayed for radioactivity associated with macromolecules, MAAs defined by antiserum SB29, or Dr antigens. All assays were performed on 0.025-ml aliquots of material in the presence of a final concentration of 0.5% NP-40.
[b]Assayed by precipitation with 10% trichloroacetic acid.
[c]Assayed by protein A-immune precipitation with specific antisera.
[d]From untreated control.

TABLE 3

Surface MAAs expressed by melanomas in various individuals

Expression of MAA in melanoma[a]

| MAA | Antiserum | HM31 | HM34 | HM49 | HM54 | HM60 | HM80 | G361 | SK23 | SK27 | SK28 | SK29 | SK37 | M14 | M20 | VAL |
|---|---|---|---|---|---|---|---|---|---|---|---|---|---|---|---|---|
| 240+ | SB29 | + | + | – | ++ | ++ | – | ++ | ++ | ++ | ++ | ++ | + | ++ | ++ | ++ |
|  | SB54 | + | + | – | + | – | – | ++ | – | – | – | – | – | – | – | – |
|  | 225.28S | – | – | – | – | ++ | ++ | – | + | – | ++ | ++ | +++ | +++ | +++ | – |
|  | 9.2.27 | – | – | + | – | ++ | ++ | + | – | + | – | – | – | ++ | – | – |
| 150 | SB29 | + | + | + | + | – | – | + | – | – | – | – | – | – | – | – |
| 140 | SB29 | ++ | ++ | + | ++ | ++ | – | ++ | – | – | – | – | – | – | – | – |
| 120 | S829 | ++ | ++ | + | ++ | ++ | ++ | ++ | – | – | – | – | – | – | – | – |
|  | SB54 | – | + | – | – | – | – | – | – | – | – | – | – | – | – | – |
| 116 | Nu4B | ++ | – | – | ++ | – | – | ++ | + | + | – | + | – | – | + | + |
| 95–97 | SB29 | ++ | + | – | ++ | ++ | ++ | ++ | – | – | – | – | – | – | – | – |
|  | SB54 | – | – | – | – | – | – | + | + | – | – | – | – | – | – | – |
|  | 118.1 | ++ | – | – | ++ | ++ | ++ | ++ | ++ | ++ | ++ | + | ++ | ++ | ++ | ++ |
| 75 | SB29 | + | + | – | + | – | – | + | + | + | ++ | ++ | + | ++ | ++ | ++ |
|  | SB54 | – | – | – | + | – | – | + | – | – | – | – | – | – | – | – |
| 70 | Mel TBT | – | – | – | – | – | – | – | – | – | – | – | – | – | – | – |

[a] Assayed by indirect immunoprecipitation with protein A-sepharose.

TABLE 4

Characteristics of immunized patients

| Patient no. | Age | Sex | Previous treatment other than surgery | Site of metastasis | Duration of metastatic disease prior to immunization (months) | No. of immunization | Current status[a] | Length of follow-up[b] (months) |
|---|---|---|---|---|---|---|---|---|
| 1 | 31 | F | BCG,[c] . DTIC | Skin, lung | 12 | 10 | P | ¼ |
| 2 | 24 | F | None | Lung | 2 | 10 | P | 3 |
| 3 | 53 | M | None | Skin | 2 | 13 |   | 8 |
| 4 | 58 | F | None | Skin | 2 | 8 | P | 1 |
| 5 | 48 | M | None | Skin | 1 | 12 | P | 3 |
| 6 | 58 | M | None | Skin | 2 | 11 | P | 3 |
| 7 | 54 | M | None | Skin | 2 | 14 | P | 4 |
| 8 | 68 | M | None | Skin, lung | 2 | 10 | P | 6 |
| 9 | 75 | F | DTIC, Actinomycin D | Skin | 36 | 17 | S | 14 |
| 10 | 46 | M | None | Skin | 1 | 18 | R | 24 |
| 15 | 29 | M | None | Skin | 4 | 8 | P | 2 |
| 17 | 68 | M | None | Skin | 4 | 8 | P | 2 |
| 20 | 38 | M | None | Skin, lung | 3 | 13 | P | 4 |

[a](P) progression; (S) stable; (R) regression.
[b]From onset of immunotherapy.
[c](BCG) bacillus Calmetie-Guérin.

TABLE 5

| Patient no. | Immune response to melanoma[a] | | |
|---|---|---|---|
|   | Humoral[b] | Cellular[c] | Either |
| 1 | ++ | 0 | 5 |
| 2 | + | 10 | + |
| 3 | + | 0 | + |
| 4 | 0 | 0 | 0 |
| 5 | ± | 5 | 0 |
| 6 | 0 | 0 | 0 |
| 7 | 0 | 0 | + |
| 8 | 0 | 0 | 0 |
| 9 | 0 | 20 | + |
| 10 | + | 10 | + |
| 15 | ++ | 0 | + |
| 17 | 0 | NT | 0 |
| 20 | NT | 25 | + |
| No. (%) positive: | 5 (38%) | 4 (31%) | 8 (62%) |

[a](±)25–49%, (+)50–100%, and (++) 100%, increase over preimmunization level of melanoma antibodies: (NT) not tested.
[b]By indirect immunoprecipitation of $^{125}$I-melanoma macromolecules.
[c]By skin test to 10 μg vaccine; results represent millimeters of average induration at 24–28 h.

TABLE 6

Antibodies to fetal calf serum proteins in patients immunized to melanoma vaccine

| Patient no. | Antibodies to preimmunization | $^{125}$I-FCS[a] (2 months postimmunization) |
|---|---|---|
| Melanoma | | |
| 1 | 18.3 | 0.7 |
| 2 | 0.0 | 0.1 |
| 3 | 0.0 | 0.0 |
| 4 | 0.1 | 0.1 |
| 5 | 0.1 | 0.2 |
| 6 | 0.1 | <0.1 |
| 7 | <0.1 | 0.1 |
| 8 | <0.1 | <0.1 |
| 9 | 0.6 | 0.8 |
| 10 | 0.0 | 0.0 |
| 15 | 0.1 | <0.1 |
| 17 | 0.3 | 0.4 |
| 20 | 0.0 | 0.0 |
| Normal | | |
| 2003 | 0.0 | |
| 2004 | 0.1 | |
| 2005 | <0.1 | |
| 2006 | 0.0 | |
| 2007 | 0.0 | |
| 2008 | 0.0 | |
| 2009 | 0.0 | |
| 2010 | 0.1 | |
| 2011 | 0.0 | |
| 2012 | 0.0 | |
| 2013 | 0.0 | |
| ANTI-FCS | 68.0 | |

[a]Percent of radioactivity associated with $^{125}$I-FCS specifically immunoprecipitated by serum and protein A-sepharose.

What is claimed is:

1. A polyvalent serum-free human melanoma vaccine useful for the treatment of human melanoma, said vaccine consisting essentially of shed human melanoma cell surface antigens recovered after culturing multiple different human melanoma cell lines for about three hours in a serum-free medium, said cell lines having been previously adapted to and maintained in a serum-free medium wherein said cell lines are selected on the basis of shedding different molecular weight melanoma associated antigens during culturing in a serum-free medium.

2. A polyvalent vaccine useful for the treatment of human melanoma cancer, said vaccine composition consisting essentially of multiple melanoma associated cell surface antigens shed upon culturing human melanoma cell lines in serum-free media for about 3 hours, said cell lines having been previously adapted to and maintained in a serum-free medium, wherein the shed cell surface antigens from multiple different cell lines are pooled.

3. A method of treating a human suffering from human melanoma cancer which comprises administering to the human a vaccine in accordance with claim 2.

4. A vaccine suitable for administration to a human for the treatment of human melanoma cancer, said vaccine consisting essentially of human melanoma associated cell surface antigens and a suitable physiologically acceptable carrier therefor, said vaccine containing said human melanoma associated antigens having been prepared by:

(a) culturing for a period of time of about three hours in a serum free medium a pool of human melanoma cells wherein said cells are selected based on shedding of different molecular weight cell surface melanoma associated antigens, said melanoma cells prior to culturing having been adapted to and maintained in a serum free culture medium;

(b) subjecting the culture medium after culturing the melanoma cells therein to a particle separation operation for the removal of melanoma cells from said culture medium;

(c) concentrating the resulting melanoma cell free culture medium which medium contains shed melanoma associated cell surface antigens therein, said antigens having been shed from said melanoma cells during culturing; and (d) recovering resulting shed melanoma cell antigens and utilizing said recovered shed antigens in the preparation of said vaccine comprising said melanoma associated cell surface antigens.

5. A method for the treatment of human melanoma which comprises administering to a human a vaccine in accordance with claim 4.

6. A method for the treatment of human melanoma which comprises intradermally administering to a human a vaccine in accordance with claim 4.

7. A method for the treatment of human melanoma which comprises intravenously administering to a human a vaccine in accordance with claim 4.

8. A method for the treatment of human melanoma which comprises intramuscularly administering to a human a vaccine in accordance with claim 4.

9. A method for the treatment of human melanoma which comprises intermittently intradermally administering to a human a vaccine in accordance with claim 4.

* * * * *